United States Patent [19]

Petró et al.

[11] 4,036,877

[45] July 19, 1977

[54] PROCESS FOR THE PRODUCTION OF ALDEHYDES

[75] Inventors: Jósef Petró; Tibor Máthé; Antal Tungler, all of Budapest, Hungary

[73] Assignee: Budapesti Muszaki Egyetem, Budapest, Hungary

[21] Appl. No.: 549,143

[22] Filed: Feb. 12, 1975

[51] Int. Cl.$^2$ .................. C07C 63/00; C07C 47/52; C07C 47/54
[52] U.S. Cl. .................. 260/515 R; 260/600 R; 260/601 R; 260/602; 260/598; 260/599; 260/601 H; 260/347.5
[58] Field of Search .............. 260/601 R, 347.5, 600, 260/602, 598, 601 H, 599, 515 R

[56] References Cited

U.S. PATENT DOCUMENTS 3,517,066  6/1970  Gurien et al. .................. 260/601 R

OTHER PUBLICATIONS

Karpova et al., Chem. Abstracts, vol. 56, 55e, 1962.
Rosenmund, K. W., Berichte, vol. 51, pp. 585-593, 1918.

*Primary Examiner*—James O. Thomas, Jr.
*Assistant Examiner*—W. B. Lone

[57] ABSTRACT

The invention relates to a process for the preparation of aldehydes by hydrogenating carboxylic chlorides of the general formula RCOCl, wherein R stands for alkyl, isoalkyl, substituted alkyl, cycloalkyl, substituted cycloalkyl, aromatic, heterocyclic or substituted heterocyclic group, the substituents being alkyl, halogen, hydroxy, alkoxy, carboxyl, carbonyl and nitro groups wherein the hydrogenation is carried out in the presence of an alloy catalyst comprising at least one element of the platinum group and at least one element of the groups IB and IIB of the periodic system.

The invention renders possible the production of aldehydes in a fair yield and at an adequate selectivity.

1 Claim, No Drawings

PROCESS FOR THE PRODUCTION OF ALDEHYDES

This invention relates to a process for the production of aldehydes by hydrogenating acid chlorides.

It is known that on hydrogenating organic acid chlorides in the presence of noble metal catalysts that are poisoned or of reduced activity, the corresponding aldehydes can be produced (Organic Reactions IV, p. 382, E. Mosettig, R. Mozinga). By this process, however, generally not only the corresponding aldehyde but also certain amount of alcohol or of other contaminant is formed. Thus, the reaction mixture has to be purified and the aldehyde yield referred to the acid chloride decreases.

In a very recent variant of the above-mentioned so-called Rosenmund process (Japanese Pat. No. 6813,204) the initial compound is salicylic chloride which is hydrogenated at 70° to 80° C in the presence of poisoned Ni, Os, Pd, or Pt catalysts. Sulphur in quinoline is employed as catalyst poison. A drawback of this process is that the reaction does not stop with the formation of salicylic aldehyde but the aldehyde is further hydrogenated to salicylic alcohol, though at a rate lower than the acid chloride. Salicylic alcohol reacts with salicylic chloride and this decreases still more the aldehyde yield.

In the Rosenmund reduction, however, mostly only palladium precipitated on barium sulphate can be employed. Consequently, the activity of the catalyst is considerably limited since it is impossible to prepare from barium sulphate a carrier of adequately great surface.

Another limiting factor of the applicability of the process is that certain acid chlorides can be hydrogenated with the poisoned catalysts only at higher temperatures (e.g. methyl succinate chloride at 110° C, naphthoic chloride at 140° C), and under such conditions also other side reactions take place in the reaction mixture and thus the yield is decreased.

This invention aims at ensuring a process rendering possible the production of aldehydes in a fair yield and at an adequate selectivity, by means of the selective hydrogenation of acid chlorides.

The invention is based on the recognition that carboxylic chlorides of the general formula RCOCl, wherein R stands for an alkyl, isoalkyl, substituted alkyl, cycloalkyl, substituted cycloalkyl, aromatic, substituted aromatic, heterocyclic, or substituted heterocyclic group, the substituents being alkyl, halide, hydroxy, alkoxy, carboxyl, carbonyl, and nitro groups, can be selectively hydrogenated to the corresponding aldehydes when an alloy catalyst is applied which contains at least one element of the metals of the platinum group and at least one element of the groups IB and IIB of the periodic system.

Accordingly, the invention is a process for the production of aldehydes by hydrogenating acid chlorides of the general formula RCOCl, wherein R stands for alkyl, isoalkyl, substituted alkyl, cycloalkyl, substituted cycloalkyl, aromatic, substituted aromatic, heterocyclic or substituted heterocyclic group, the substituents being alkyl, halogen, hydroxy, alkoxy, carboxy, carbonyl, and nitro groups, into the corresponding aldehydes, wherein the solution of the acid chloride of the general formula RCOCl is reacted with hydrogen in the presence of an alloy catalyst comprising at least one element of the platinum group and at least one element of groups IB and IIB of the periodic system.

The alloy catalyst contains preferably at least one element of the group consisting of palladium, platinum, rhodium and osmium, and at least one element of the group consisting of copper, silver, gold, cadmium, and mercury.

The catalyst is preferably used on a carrier. Of the carriers that proved to be favourable, activated carbon, silica, alumina and calcium carbonate can be mentioned. To 1–10% by weight of the element of the platinum group, 0.01 to 5% by weight of an element of the group IB and/or IIB of the periodic system was alloyed and the alloy transferred onto the carrier.

According to a preferred embodiment of the invention a solution of the acid chloride of the general formula RCOCl in benzene, toluene or xylene is reacted with hydrogen in the presence of a catalyst containing 2 to 5% by weight of palladium and 0.1 to 3% by weight of copper on activated carbon as carrier, at a temperature of 0° to 190° C, preferably 40° to 150° C and at a pressure of 1 to 50 atm., preferably 1 to 10 atm.

Of the main advantages of the process according to the invention the following are mentioned:

a. It renders possible to the production of aldehydes in a fair yield and at an adequate selectivity by the hydrogenation of acid chlorides.

b. During the hydrogenation process the decomposition of the starting material is of a small extent, and side reactions take place only in a slight degree.

c. It is not necessary to use poisoned catalysts, whereby the process is considerably simpler than the known ones.

d. The catalyst can be prepared in a simple way, it can be employed consecutively several times and it can be regenerated.

e. The catalyst is only slightly pyrophoric, and thus no special measures are required when it is applied under industrial conditions.

The process according to the invention is further illustrated by the following non-limiting Examples.

EXAMPLE 1

95 g. of activated carbon of fine grain was purified for 2 hours at a temperature of 100°–120° C in a vacuum of 20 torr and then impregnated with a solution of 7.5 g. of $PdCl_2$ and 0.537 g. of $CuCl_2 \cdot 2H_2O$ in 8 ml. of concentrated hydrochloric acid to prepare a catalyst containing 4.5% by weight of palladium and 0.2% by weight of copper. The impregnated carrier was neutralized and washed with distilled water and subsequently reduced with hydrogen or sodium borohydride. After washing the catalyst to neutrality it was dried. The operation could be carried out without any special measures since the obtained catalyst was pyrophoric to a reduced extent only.

6 g. of the catalyst prepared in this way was transferred into a flask equipped with a stirrer and a gas inlet tube. On adding 200 ml. of xylene, hydrogen was allowed to bubble through the liquid at a rate of 30 liters/hour, and under intensive stirring 25 g. of salicylic chloride was added at 70° C. The temperature was raised within 30 minutes to 83° C and bubbling of hydrogen was continued until the development of HCl gas was terminated (for about 4–5 hours). The catalyst was filtered off the reaction mixture, the solvent was evaporated and the aldehyde distilled in vacuum. The amount of the pure product was 15.6 g., corresponding to a yield of 80%.

EXAMPLE 2

The catalyst was prepared in the way described in Example 1, with the difference that the impregnating solution contained 8.35 g. of $PdCl_2$ and 0.67 g. of $CuCl_2 \cdot 2H_2O$ to obtain a catalyst with a palladium content of 5% by weight and a copper content of 0.25% by weight. On weighing 7 g. of this catalyst, the procedure was the same as described in Example 1, the hydrogenation of 25 g. of salicylic chloride being carried out at 85° C for 6 hours. The reaction mixture was processed and the product separated in the way described in Example 1. The pure product weighed 16.2 g., corresponding to a yield of 83%.

EXAMPLE 3

The catalyst was prepared in a way similar to that described in Example 1, with the difference that the impregnating solution contained 0.21 g. of $AuCl_3$ in addition to 2.43 g. of $PdCl_2$ and the prepared catalyst contained 1.5% by weight of palladium and 0.14% by weight of gold.

On weighing 10 g. of this catalyst, the solution of 25 g. of salicylic chloride in xylene was hydrogenated for 8 hours in the way described in Example 2. The obtained end product weighed 15 g., corresponding to a yield of 77%.

EXAMPLE 4

The catalyst described in Example 3 was modified so that the catalyst on a carrier of activated carbon contained 2% by weight of palladium, 0.4% by weight of gold and 0.2% by weight of copper.

The impregnating solution applied to prepare this catalyst contained 3.28 g. of $PdCl_2$, 0.604 g. of $AuCl_3$ and 0.528 g. of $CuCl_2 2H_2O$.

On preparing a suspension of 5 g. of this catalyst in 30 ml of acetone, the suspension was saturated with hydrogen at a pressure of one atmosphere. Subsequently, 10 ml. of dimethyl acetamide and 20 g. of 2,4,6-trimethoxybenzoyl chloride dissolved in 30 ml. of acetone were added. Hydrogenation was carried out at room temperature at atmospheric pressure. On continuing hydrogenation for 3 hours, the mixture was filtered, evaporated to one third of the initial volume, and poured into 100 ml. of a saturated solution of sodium hydrogen carbonate. The crystallized aldehyde was filtered off, washed with distilled water and then dried. The product weighed 13.6 g., corresponding to a yield of 80%.

EXAMPLE 5

In this Example a catalyst was employed which contained 4% by weight of palladium, 1% by weight of platinum and 0.5% by weight of copper on activated carbon as carrier. This catalyst was prepared in a way similar to that described in Example 1, using an impregnating solution containing 6.67 g. of $PdCl_2$, 2.655 g. of $H_2PtCl_6 \cdot 6H_2O$ and 1.34 g. of $CuCl_2 \cdot 2H_2O$.

On preparing a suspension of 5 g. of this catalyst in 200 ml. of xylene, 30 g. of benzoyl chloride were added to the suspension after prehydrogenation. Then hydrogenation was carried out in the way described in Example 1, with the difference that the temperature was 65° C. On continuing hydrogenation for 8 hours, the mixture was processed as described in Example 1. In this way 19.3 g. of benzaldehyde were obtained, corresponding to a yield of 85%.

EXAMPLE 6

With the method described in Example 1, a catalyst containing 1% by weight of rhodium and 0.15% by weight of copper on activated carbon as carrier was prepared, using an impregnating solution containing 1.98 g. of $RhCl_3$ and 0.396 g. of $CuCl_2 \cdot 2H_2O$.

Then 2,4,6-trimethoxybenzoyl chloride was hydrogenated with 5 g. of this catalyst in the way described in Example 4. The obtained aldehyde weighed 12.4 g., corresponding to a yield of 73%.

EXAMPLE 7

With the method described in Example 1, a catalyst containing 1% by weight of osmium and 0.18% by weight of silver on activated carbon as carrier was prepared using an impregnating solution containing 2.25 g. of $(NH_4)_2OsCl_6$ and 0.280 g. of $AgNO_3$. With 7 g. of this catalyst in a xylene suspension, 25 g. of salicylic chloride were hydrogenated in the way described in Example 1, at 90° C. Hydrogenation was continued for 8 hours. The obtained product weighed 13.6 g., corresponding to a yield of 70%.

EXAMPLE 8

With the method described in Example 1, but using an impregnating solution containing 5.45 g. of $H_2PtCl_6 \cdot 6H_2O$ and 0.215 g. of $CuCl_2 \cdot 2H_2O$, a catalyst containing 2% by weight of platinum and 0.08% by weight of copper on activated carbon as catalyst was prepared.

On preparing a suspension of 7 g of this catalyst in 200 ml. of toluene, 30 g. of ortho-chlorobenzoyl chloride were added to the suspension, and hydrogenation was carried out at 50° C by allowing hydrogen to bubble through the suspension at a rate of 30 liters/hour. On continuing hydrogenation for 7 hours, the catalyst was filtered off the mixture, toluene was distilled off, then the aldehyde was distilled in a vacuum of 20 torr. The product was 18.1 g. of ortho-chlorobenzaldehyde, corresponding to a yield of 75%.

EXAMPLE 9

With the method described in Example 1, but using an impregnating solution containing 7.45 g. of $PdCl_2$ and 0.268 g. of $CuCl_2 \cdot 2H_2O$, a catalyst containing 4.5% by weight of palladium and 0.1% by weight of copper was prepared.

With 7 g. of this catalyst 30 g. of meta-nitrobenzoyl chloride were hydrogenated in a xylene solution at 120° C, in a way similar to that described in Example 1. The amount of aldehyde purified by distillation was 20.8 g., corresponding to a yield of 85%.

EXAMPLE 10

With the method described in Example 1, but using an impregnating solution containing 7.45 g. of $PdCl_2$ and 0.134 g. of $CuCl_2 \cdot 2H_2O$, a catalyst containing 4.5% by weight of palladium and 0.05% by weight of copper was prepared.

With 5 g. of this catalyst 20 g. of butyryl chloride were hydrogenated in an ethereal solution at 30° C, in a way similar to that described in Example 1. The amount of aldehyde purified by distillation was 9.1 g., corresponding to a yield of 67%.

EXAMPLE 11

With the method described in Example 1, but using an impregnating solution containing 7.5 g. of $PdCl_2$ and 0.805 g. of $CuCl_2 \cdot 2H_2O$, a catalyst containing 4.5% by weight of palladium and 0.3% by weight of copper was prepared.

With 8 g. of catalyst prepared in this way, 30 g. of para-phthalyl chloride were hydrogenated at 125° C in the way described in Example 1. The yield calculated from the bisulphite adduct of the aldehyde was 83%.

EXAMPLE 12

With the method described in Example 1, but using an impregnating solution containing 7.5 g. of $PdCl_2$ and 0.59 g. of $CuCl_2 \cdot 2H_2O$, a catalyst containing 4.5% by weight of palladium and 0.22% by weight of copper was prepared.

With 7 g. of this catalyst, 30 g. of furanoyl chloride were hydrogenated at 70° C in a way similar to that described in Example 1. The amount of distilled 3-furanoyl aldehyde was 13.3 g., corresponding to a yield of 60%.

EXAMPLE 13

The catalyst was prepared in the way described in Example 1, with the difference that the solution contained 8.35 g. of $PdCl_2$ and 0.86 g. of $ZnCl_2$ to obtain a catalyst product containing 5% by weight of palladium and 0.30by weight of zinc.

On weighing 7 g. of this catalyst, the procedure described in Example 1 was followed, and 25 g. of salicylic chloride were hydrogenated at 85° C for 4 hours. The reaction mixture was processed and the product separated in the way described in Example 1. The pure product weighed 16.6 g., corresponding to a yield of 85%.

EXAMPLE 14

The catalyst was prepared in the way described in Example 1, with the difference that the solution contained 8.35 g. of $PdCl_2$ and 0.895 g. of $CdCl_2$ to obtain a catalyst product containing 5% by weight of palladium and 0.55% by weight of cadmium.

With 7 g. of this catalyst, 25 g. of salicylic chloride were hydrogenated for 3 hours in the way described in Example 1. The pure salicylic aldehyde weighed 16.2 g., corresponding to a yield of 83%.

EXAMPLE 15

With the method described in Example 1, but using an impregnating solution containing 7.5 g. of $PdCl_2$ and 1.08 g. of $HgCl_2$, a catalyst containing 4.5% by weight of palladium and 0.8% by weight of mercury was prepared.

With 8 g. of this catalyst, benzoyl chloride was hydrogenated in the way described in Example 5. On processing the mixture after hydrogenating for 5 hours, the obtained benzaldehyde weighed 18.4 g., corresponding to a yield of 81%.

EXAMPLE 16

A catalyst containing 5% by weight of palladium and 0.25% by weight of zinc was prepared as described in Example 1, using an impregnating solution containing 8.35 g. of $PdCl_2$ and 0.715 g. of $3nCl_2$.

With 10 g. of this catalyst, 30 g. of γ-chlorobutyrylchloride were hydrogenated in 200 ml. of benzene at 55° C for 5 hours. On subjecting the reaction mixture to fractional distillation, 14.7 g. of γ-chlorobutyraldehyde and 2.5 g. of cyclobutanone were obtained. The yield of the aldehyde was 65%.

What is claimed is:

1. In a process for the preparation of aldehydes by hydrogenating carboxylic acid chlorides of the general formula RCOCl wherein R stands for phenyl or substituted phenyl group, the substituents being alkyl, halogen, hydroxy, alkoxy, carboxyl, carbonyl or nitro groups, the improvement which comprises conducting the hydrogenating reaction in the presence of an alloy catalyst consisting of at least one element of the platinum group and selected from the group consisting of palladium, platinum, rhodium, and osmium, and at least one element of the groups IB and IIB of the periodic system and selected from the group consisting of copper, silver, gold, cadmium, and mercury, on a carrier selected from the group consisting of activated carbon, silica, alumina and calcium carbonate at a temperature from about 0° to 190° and at a pressure of about 1 to 50 atmospheres.

* * * * *